(12) United States Patent
Soper

(10) Patent No.: US 6,513,171 B1
(45) Date of Patent: Feb. 4, 2003

(54) ACTIVITY EYE WEAR

(75) Inventor: John C. Soper, Houston, TX (US)

(73) Assignee: Soper Enterprises, Inc., Houston, TX (US)

( * ) Notice: Subject to any disclaimer, the term of this patent is extended or adjusted under 35 U.S.C. 154(b) by 0 days.

(21) Appl. No.: 09/705,568

(22) Filed: Nov. 3, 2000

(51) Int. Cl.[7] .................................................. A61F 9/02
(52) U.S. Cl. ............................................. 2/436; 351/43
(58) Field of Search .......................... 2/439, 441, 446, 2/426, 445, 454, 436; 351/41, 43, 44, 60, 132, 138

(56) References Cited

U.S. PATENT DOCUMENTS

| | | | |
|---|---|---|---|
| D177,581 S | 5/1956 | Moeller | |
| 3,931,646 A | * 1/1976 | Loughner | ........................ 2/14 |
| 4,043,637 A | 8/1977 | Hovey | |
| 4,571,748 A | * 2/1986 | Carroll et al. | ................. 2/436 |
| D299,356 S | 1/1989 | Lyons | |
| 4,852,189 A | 8/1989 | Duggan | |
| D309,619 S | 7/1990 | Kalbach | |
| 4,951,322 A | 8/1990 | Lin | |
| D323,665 S | 2/1992 | Simioni | |
| D354,972 S | 1/1995 | Hirschman | |
| 5,390,369 A | * 2/1995 | Tubin | .............................. 2/12 |
| 5,428,407 A | 6/1995 | Sheffield | |
| 5,740,556 A | * 4/1998 | Brown | ......................... 2/181 |
| 5,841,505 A | * 11/1998 | Bollé | ......................... 351/44 |
| D403,346 S | 12/1998 | Roberts | |
| 6,092,897 A | * 7/2000 | Smerdon, Jr. | ................ 351/157 |
| 6,247,811 B1 | * 6/2001 | Rhoades | ..................... 351/156 |

OTHER PUBLICATIONS

Web pages of xsop.com, Aug. 1, 2000, 4 sheets.
Eye protector first publicly shown, on or about Mar. 15, 2000.

* cited by examiner

Primary Examiner—John J. Calvert
Assistant Examiner—Katherine Moran
(74) Attorney, Agent, or Firm—Bracewell & Patterson, L.L.P.

(57) ABSTRACT

Activity eye wear includes brow bar member, at least one lens, and retainer cord member, with the eye wear not including conventional bow, or temple, pieces.

18 Claims, 3 Drawing Sheets

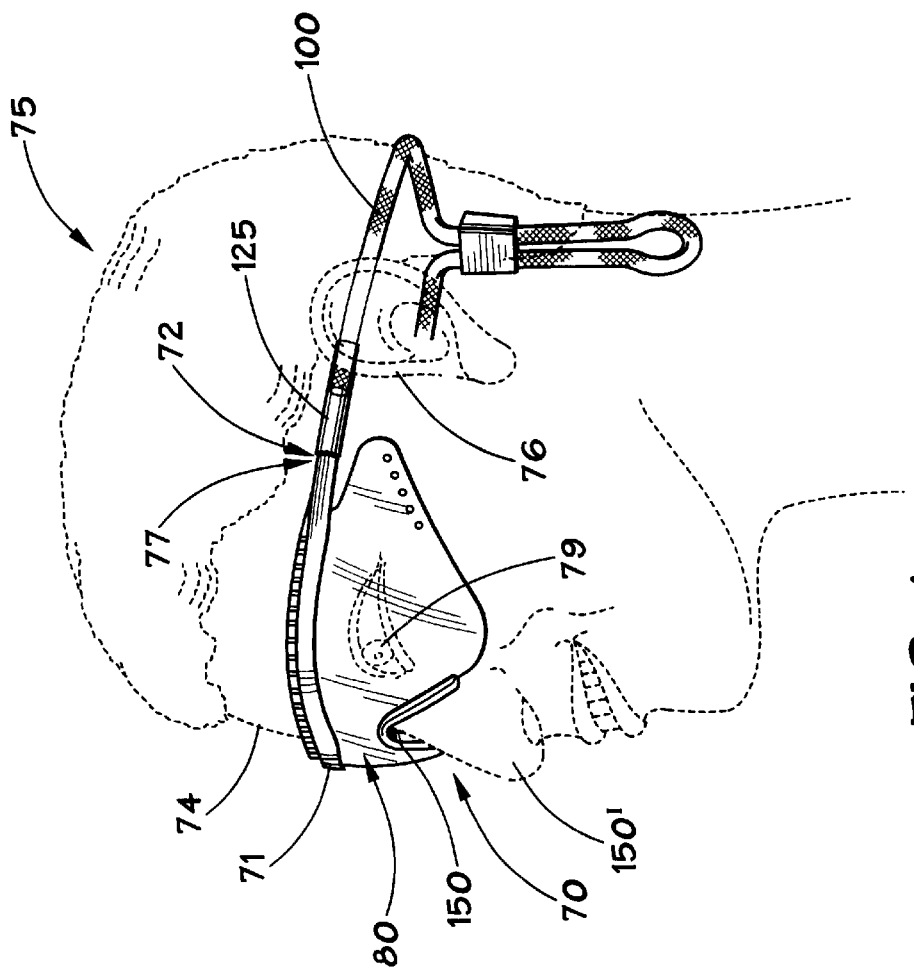
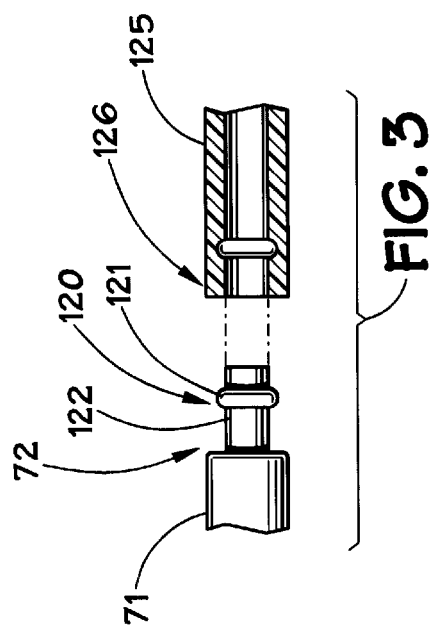
FIG. 3
FIG. 4

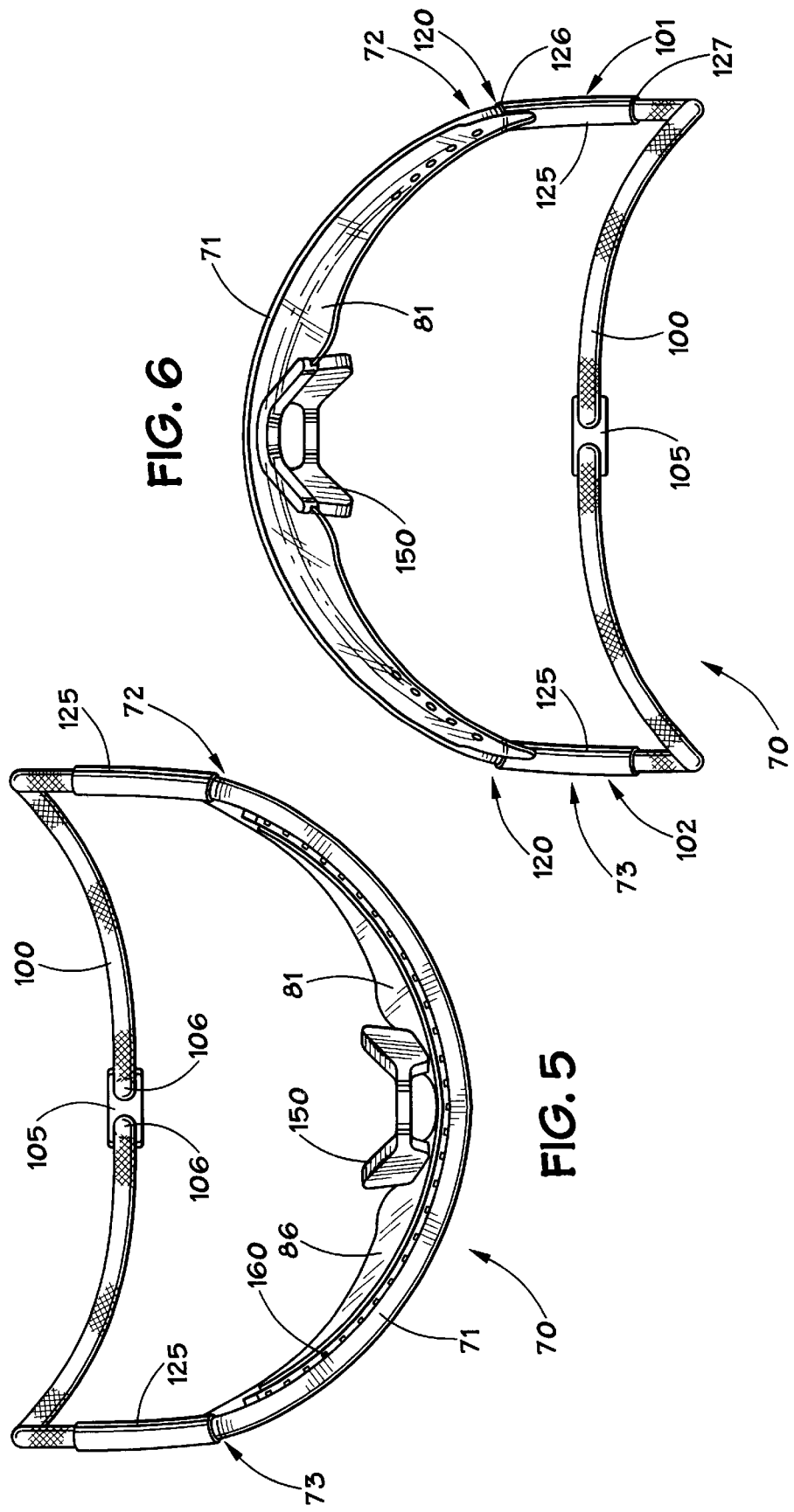

ACTIVITY EYE WEAR

FIELD OF THE INVENTION

The present invention relates to eye wear, including, but not limited to, activity eye wear, intended to be worn by individuals involved in sports and industrial activities.

DESCRIPTION OF THE RELATED ART

Conventional eye wear, including safety glasses, sun glasses, and reading glasses, among others, generally include a front frame member in which the lenses are secured, and a pair of bow, or temple, members, or temples, which are pivotally secured to the frame member. Generally, the bows, or temples, rest upon the ears of the wearer of the eye wear, and the bows, or temples, are generally curved downwardly so that they act to secure the eye wear to the head of the person wearing the eye wear. Some conventional eye wear utilize a frame member which is curved, to generally conform to the shape of the front of the person's head wearing the eye wear, such eye wear further including conventional bows or temples, as previously described.

One of the disadvantages associated with such conventional eye wear is that such eye wear is generally not designed to be "one size fits all", in that the frame members and bows or temples are manufactured in different sizes to accommodate different sizes of heads. Another disadvantage associated with conventional eye wear is that the stability of the eye wear upon a person's head is greatly affected by the intensity of the activity of the wearer. For example, a person sitting at his, or her, desk and engaging in an activity such as reading a book, generally does not have a problem with his, or her, eye wear becoming unstable and slipping off their head. In sharp contrast, an individual participating in a vigorous sports activity (such as baseball, basketball, football, hockey, running, rollerblading, shooting, hunting, skateboarding, skydiving, soccer, snow skiing and/or wind surfing) generally has a problem with their eye wear bouncing upon their head, or falling off their head. One solution for such a problem has been attaching an elastic strap to the ends of the temples of the eye wear to attempt to hold the eye wear in place during such vigorous activity. Generally, in order for such straps to work, they must exert a fair amount of pressure, or force, in order to hold the eye wear in place, which force or pressure can lead to discomfort when wearing eye wear which includes such elastic straps. Even if conventional eye wear is secured in place with the foregoing elastic strap, in many instances, such eye wear is worn by a person who is also wearing some type of hat or a helmet, such as a football helmet, or baseball batting helmet, as well as other types of protective helmets worn in other sports. In general, such conventional eye wear whether with or without an elastic restraining strap, is not generally compatible for use with other hats or such helmets, because in general, such hats and/or helmets apply pressure to the bows, or temples, of such eye wear, which may lead to severe discomfort when wearing the eye wear in combination with a helmet.

In an industrial setting, many individuals wear safety goggles, which generally are held in place by an elastic strap, which again can cause discomfort to the wearer of such safety goggles. Additionally, conventional safety goggles have their lenses mounted in a flexible frame and the frame generally includes a housing which engages the front of the person's face wearing the goggles, and generally seal the safety goggles along the wearer's forehead, nose, and around the eyes of the wearer. Wearing of such safety goggles during strenuous activities, or in hot weather, many times leads to the lenses becoming fogged up from temperature differentials, as well as having problems encountered from the wearer sweating into the safety goggles.

Accordingly, prior to the development of the present invention, there has been no eye wear, in particular, activity eye wear, which: doesn't require different sized frames and temple members; remains stable on the head of the wearer during strenuous physical activity; remains stable on the wearer without exerting undue, uncomfortable pressure upon the head of the wearer; is compatible with, and comfortable to wear, with protective helmets and hats; and does not readily fog up during use. Therefore, the art has sought eye wear which: doesn't require different sizes of frames and temple members; remains stable during strenuous activity; remains stable upon the wearer's head without the use of an elastic strap; is compatible with different types of protective helmets and hats; and does not easily fog up during use.

SUMMARY OF THE INVENTION

In accordance with the invention, the foregoing advantages have been achieved through the present eye wear. The present invention includes a brow bar member, having first and second ends, adapted to be disposed adjacent the forehead of a person wearing the eye wear, with each of the first and second ends of the brow bar member adapted to be disposed in a spaced, non-abutting relationship with each of the ears of the person wearing the eye wear; at least one lens disposed adjacent the brow bar member; each of the first and second ends of the brow bar member having a connector portion associated therewith; and an elongate cord retainer member having first and second ends, the cord retainer member having a generally rounded cross-sectional configuration, each of the first and second ends of the cord retainer member being connected to a connector portion of the brow bar member.

A further feature of the present invention is that the brow bar member may be curved, whereby the brow bar member closely conforms to the shape of the forehead of the person wearing the eye wear; and a cord retainer member is flexible and is adapted closely to conform to the shape of the temples of the person wearing the eye wear. An additional feature of the present invention is that a sweat bar member may be disposed on the brow bar member, and is adapted to be disposed in an abutting relationship with the forehead of the person wearing the eye wear.

Another feature of the present invention is that the at least one lens may be curved, whereby the at least one lens closely conforms to the shape of the forehead of the person wearing the eye wear. A further feature of the present invention is that the at least one lens may be a single lens disposed, and extending, over both eyes of the person wearing the eye wear. A nose piece member may be associated with the at least one lens. An additional feature of the present invention is that the at least one lens may include at least one vent to prevent fogging of the lens during use thereof. Additional features of the present invention are that the at least one lens may be formed of a plain glass material, or a plastic material, including a polycarbonate type of material. Additionally, the at least one lens may be a prescription lens, or may include a prescription lens attached to the at least one lens.

Another feature of the present invention is that one of the connector portions associated with the brow bar member may be an annular flange disposed upon a reduced neck portion formed on one of the ends of the brow bar member, or it may be a barbed member formed on one of the ends of the brow bar member. An additional feature of the present invention is that a flexible tubular shaped member, having first and second ends, may be associated with a connector portion of the brow bar member and one of the ends of the cord retainer member. The cord retainer member may be substantially non-elastic. A further feature of the present invention is that the cord retainer member may include a releasable locking member disposed intermediate the first and second ends of the cord retainer member, and is adapted to permit at least a portion of the cord retainer member to closely conform, in an abutting relationship, to the temples and the back of the head of the wearer of the eye wear.

The eye wear of the present invention, when compared with previously proposed conventional eye wear, has the advantages of: being generally a "one size fits all" eye wear, not requiring different sizes of bow or temple members, and, in fact, does not utilize a plurality of bow or temple members; remaining stable upon the wearer's head during strenuous activity; remaining stable upon the wearer's head without the use of an uncomfortable elastic strap; being compatible with various types of protective helmets and hats; and not easily fogging up during strenuous activity of the wearer.

BRIEF DESCRIPTION OF THE DRAWING

In the drawing:

FIG. 3 is a partial cross-sectional view of another embodiment of a connector portion;

FIG. 4 is a perspective view of the eye wear of FIG. 1, shown upon a wearer in phantom lines FIG. 5 is a top view of the eye wear of the present invention; and FIG. 6 is a bottom view of the eye wear of the present invention.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
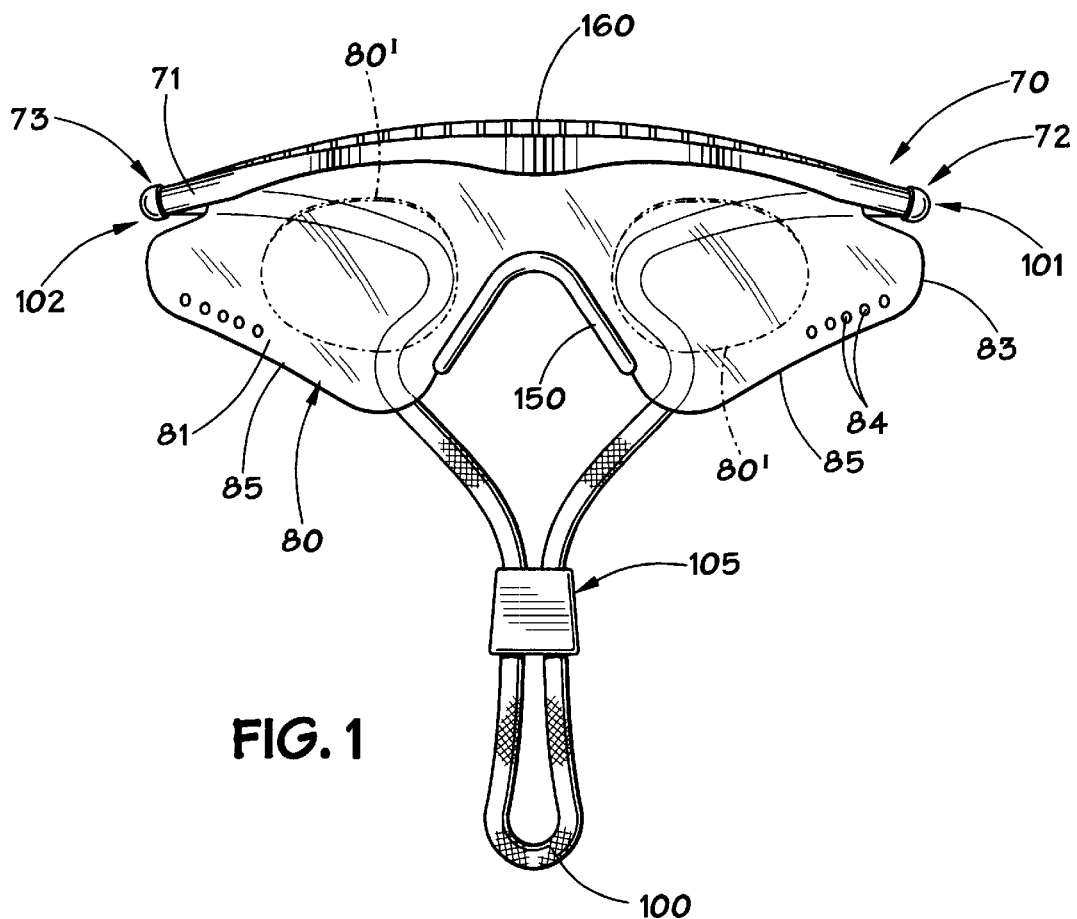
FIG. 1 is a front view of eye wear in accordance with the present invention.
Figure 2:
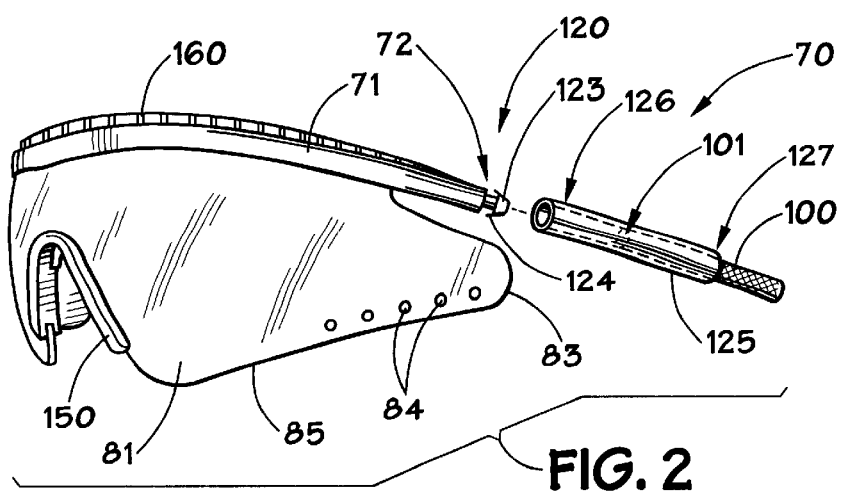
FIG. 2 is a perspective view of the eye wear of FIG. 1, the cord retainer member being separated from the brow bar member to illustrate a particular embodiment of a connector portion.

In FIGS. 1, 2, 4, and 5, eye wear, or activity eye wear, 70 is illustrated. Eye wear 70 generally includes: a brow bar member 71, having first and second ends 72, 73; at least one lens 80; and an elongate cord retainer member 100. Brow bar member 71 is generally adapted to be disposed adjacent the forehead 74 of the person 75 (FIG. 4) wearing eye wear 70. As seen in FIG. 2 the first end 72 of brow bar member 71 is shown disposed in a spaced, non-abutting relationship with the ear 76 (FIG. 4) of the person 75 wearing eye wear 70. Similarly, the other end 73 of brow bar member 71 is similarly disposed in a spaced, non-abutting relationship with the other ear (not shown) of the person wearing eye wear 70. In general, it should be noted that eye wear 70 does not include conventional bow, or temple, members as are found in conventional eye wear, previously described. In this regard, with the elimination and non-utilization of a conventional bow, or temple, member, the cord retainer member 100 is directly associated with the first and second ends 72, 73 of brow bar member 71.

With reference to FIGS. 5 and 6, it is seen that brow bar member 71 is preferably curved, whereby the brow bar member 71 will closely conform to the shape of the forehead 74 (FIG. 4) of the person 75 wearing eye wear 70. Similarly, as will hereinafter be discussed, cord retainer member 100 is preferably flexible and is also adapted to closely conform to the shape of the temples 77 (FIG. 4) of the person 75 wearing eye wear 70. As will hereinafter be described in greater detail in connection with FIGS. 2 and 3, the first and second ends 72, 73 of brow bar member 71 each preferably have a connector portion 120 associated therewith. Brow bar member 71 may be made of any suitable material having the requisite strength characteristics to function in the manner described herein, including any of a number of conventional plastic or metallic materials. Brow bar member 71 may have any desired cross-sectional shape, such as round, oval, elliptical, square, rectangular, etc.

Elongate cord retainer member 100 includes first and second ends 101, 102 and cord retainer member 100 preferably has a generally rounded cross-sectional configuration. In this regard, the term "generally rounded cross-sectional configuration" is intended to encompass the use of circular shaped, oval shaped, elliptical shaped, square-shaped, hexagonal-shaped, and other similar cross-sectional configurations. The use of the term "generally rounded cross-sectional configuration" is intended to expressly exclude conventional, elastic strap members having a generally rectangular shaped configuration wherein the width of the strap member is substantially less than the height of the strap member when viewed in a cross-sectional view. It is believed that the use of such an elongate cord retainer member 100 having a generally rounded cross-sectional configuration provides a comfortable fit for eye wear 70, without causing any discomfort during use of eye wear 70. Cord retainer member 100 may be formed of any suitable material having the requisite strength and durability characteristics to function in the manner described herein to retain eye wear 70 upon the head 78 (FIG. 2) of the person 75 wearing eye wear 70 of the present invention. Preferably, cord retainer member 100 is formed of flexible nylon, cotton, leather, or polyester material, or other materials having similar characteristics. Preferably, cord retainer member 100 is formed of Nylon and is not formed of a substantially elastic material.

Still with reference to FIGS. 1, 2, 4, and 5, it is seen that the at least one lens 80 is disposed adjacent the brow bar member 71. Lens 80 may be disposed adjacent to brow bar member in any desired manner. Preferably, lens 80 is disposed adjacent brow bar member 71 by connecting it to brow bar member 71 by a suitable glue or adhesive, or by heat sealing it to the brow bar member. Alternatively, lens 80 may be secured by any conventional connection, including screws, rivets, or other fasteners or by forming lens 80 integrally with brow bar member 71. Preferably, the at least one lens 80 is curved, whereby the at least one lens closely conforms to the shape of the forehead 74 of the person 75 wearing eye wear 70, in a slightly spaced relationship from the face of the person 75, to permit air to flow between the person's face and eye wear 70, as seen in FIGS. 2, 4, and 5. Preferably, both brow bar member 71 and the at least one lens 80 are curved as illustrated in FIGS. 5 and 6.

Preferably the at least one lens 80 is a single lens 81 disposed over, and extending over, both eyes 79 of the person 75 wearing eye wear 70. Preferably, the curved shape of brow bar member 71 and the single lens 81 not only permit lens 81 and brow bar member 71 to closely conform to the shape of the forehead 74 of the person 75 wearing eye wear 70, but also insure that eye wear 70 will be disposed in close proximity to the eyes 79 (FIG. 4) to provide protection thereto, as will hereinafter discussed in greater detail, as well as to permit the person 75 wearing the eye wear 70 to also easily wear a protective helmet, such as a baseball batter's helmet, or other type of hat (not shown).

The general shape of the at least one lens 80, or single lens 81, may be any desired shape, provided the lens is disposed over, and extends over, both eyes 79. If desired, as shown in FIGS. 1 and 2, the ends 82, 83 of the single lens 81 may extend beyond the facial bones around the eye, to end generally adjacent the ends 72, 73 of brow bar member 71. If desired, at least one lens 80 may be provided with at least one vent, and preferably a plurality of vents 84 which provide for air flow circulation between the at least one lens 80 and the person 75 wearing eye wear 70, to prevent fogging of the lens 81 during use. The vents 84 may be disposed in any desired location, a preferred location being along the lower edge 85 of the at least one lens 80, adjacent ends 82, 83 of lens 80.

Still with reference to FIGS. 1, 2, 4 and 5, it is seen that eye wear 70 may be provided with a nose piece member 150, which is adapted to rest upon the nose 150 (FIG. 4) of the person 75 wearing eye wear 70. Nose piece member 150 may be of any desired design, but preferably is of one piece construction disposed intermediate the ends 82, 83 of lens 81. Nose piece 150 may be made of any suitable plastic material, including rigid or flexible plastic materials, as well as foamed plastic materials, which can provide additional cushioning between lens 80 and the nose of the person 75 wearing eye wear 70. Although the at least one lens 80 is illustrated to preferably be a single lens 81, it should be noted that the at least one lens 80 could be two individual lenses (not shown) which would preferably be associated with brow bar member 71 in a similar manner as is illustrated and described in connection with single lens member 81.

The at least one lens 80 may be formed of a plain glass material, as is known in the art, and the glass material may be clear, tinted, or coated, as is known in the art. If desired, the at least one lens 80 can be a prescription lens, or a prescription lens (80) may be secured in any suitable fashion to the inner surface 86 (FIG. 5) of the at least one lens 80 in any suitable manner. Alternatively, the at least one lens 80, as well as the single lens 81, may be formed of a plastic lens material as are known in the art. Preferably, if eye wear 70 is intended to be worn by a person 75 engaged in sporting activities, wherein protection is desired from various types of projectiles, such as baseballs, fishing lures, golfballs, hockey pucks, etc. or in an industrial setting wherein protection is desired against projectiles such as metal chips and shavings, etc. the at least one lens 80 is formed of a polycarbonate plastic material, which preferably may have a thickness of approximately 2 mm. This type of plastic material has been designed to afford better protection to the eyes and facial bones of an individual to minimize damage occurring from projectiles, such as those previously described, or from other types of high velocity objects aimed towards the head, face, and/or eyes of a person. While it is believed that the use of such a polycarbonate material affords better protection than other known materials used for eye wear, it should be noted that no lens materials, as well as no eye wear, protective or otherwise, can afford complete protection of a person's eyes and facial bones against damage occurring from the foregoing described projectiles and/or high velocity objects aimed toward the head, face, and eyes. Accordingly, it is always up to the person using any type of eye wear to exercise due care and caution when participating in any activity that could subject and expose the person to projectiles or high velocity objects, including those wearing eye wear in an industrial setting. Additionally, if desired, the at least one lens 80 may be made of a material which absorbs ultraviolet light/solar radiation, in order to afford protection to the wearer's eyes, or alternatively, the material forming the at least one lens 80 could be treated to provide such protection against ultraviolet light/solar radiation.

With reference to FIGS. 1, 2, 4, and 5, eye wear 70 may be provided with a sweat bar member 160 disposed on the inner surface of the brow bar member 71, and is thus adapted to the disposed in an abutting relationship with the forehead 74 of the person 75 wearing eye wear 70. The sweat bar member 160 may be made of any suitable material, provided it has the requisite characteristics to absorb sweat from the person 75 wearing eye wear 70. For example, sweat bar member 160 can be made of any suitable fabric or plastic material, including various types of foamed plastic materials. Additionally, sweat bar member 160 may afford additional cushioning between brow bar member 71 and the forehead 74 of the person 75 wearing eye wear 70.

With reference to FIGS. 2 and 3, connector portions 120 associated with the brow bar member 71 are shown. In FIG. 3, connector portion 120 is illustrated as being an annular flange 121 disposed upon a reduced neck portion 122 disposed at the end 72 of brow bar member 71. The connector portion 120 shown in FIG. 2 is illustrated as being a barbed member 123 formed on a reduced neck portion 122, disposed at the end 72 of brow bar member 71. A flexible tubular shaped member 125 having first and second ends 126, 127 may be associated with connector portion 121, as by disposing connector portion 121, 123 within the first end 126 of the tubular shaped member 125, as shown in phantom lines in FIG. 3. In the case of the connector portion 120 of FIG. 3, frictional forces resulting from the interference fit of the annular flange 121 within tubular shaped member 125 secures tubular shaped member 125 to brow bar member 71. In the case of the barbed member 123 of FIG. 2, the barbs of the barbed member 123 permit the tubular shaped member 125 to be slid over the barbed member 123 of connector portion 120, and the barbs 124 then engage the interior of the tubular shaped member 125, precluding movement of tubular shaped member 125 away from brow bar member 71, so as to prevent inadvertent separation between tubular shaped member 125 and brow bar member 71. As shown in the drawing, and particularly in FIG. 3, tubular shaped member 125 and brow bar member 71 and connector portion 120 may be sized, if desired, so that when tubular shaped member 125 abuts against brow bar member 71, the outer surface of brow bar member 71 and tubular shaped member 125 lie in the same plane, and present a smooth connection.

Still with reference to FIGS. 2 and 3, it is seen that the ends 101, 102 of cord retainer member 100 are received within the second end 127 of tubular shaped member 125, so that cord retainer member 100 is secured to brow bar member 71 via the tubular shaped member 125 and connector portions 120. The ends 101, 102 of cord retainer member 100 may be secured within tubular shaped member 125 in any suitable manner, such as by the use of a suitable adhesive or glue, by heat sealing, by a friction fit, or any other suitable manner. Preferably, tubular shape members 125 are formed of a suitable flexible plastic material, which permits the insertion of connector portion 120 and the ends of the cord retainer member 100 into tubular shaped members 125.

With reference to FIG. 1, cord retainer member 100 may include a releasable locking member 105 disposed intermediate first and second ends 101, 102 of cord retainer member 100, and releasable locking member 105 is adapted to permit at least a portion of the cord retainer member 100 to closely conform, in an abutting relationship to the temples 77 and the back of the head of the wearer 75 of eye wear 70, as shown in FIG. 2. Preferably, releasable locking member 105 is formed of a suitable plastic material, having two openings, or passageways, 106 (FIG. 6) extending there through, and releasable locking member 105 frictionally engages the cord retainer member 100 to insure the proper fit of eye wear 70 in a stable and secure manner to the person 75 wearing eye wear 70. The wearer 75 may hold locking member 105 in one hand, and pull retainer cord member 100 to tighten a portion of cord retainer member 100 about the back of the wearer's head, and the frictional engagement between locking member 105 and cord retainer member 100 provides the correct, secure, and comfortable fit of eye wear 70 upon the wearer's head.

It is to be understood that the invention is not limited to the exact details of construction, operation, exact materials or embodiment shown and described, as obvious modifications will be apparent to one skilled in the art. For example, the connector portions on the brow bar member, may merely be the ends of the brow bar member, which are inserted into the tubular shaped members to thus attach the cord retainer member to the brow bar member. Accordingly, the invention is therefore to be limited only by the scope of the appended claims.

I claim:

1. Eye wear, comprising:
    a brow bar member, having first and second ends, adapted to be disposed adjacent the forehead of a person wearing the eye wear, with each of the first and second ends of the brow bar member adapted to be disposed in a spaced, non-abutting relationship with each of the ears of the person wearing the eye wear;
    at least one lens disposed adjacent the brow bar member; each of the first and second ends of the brow bar member having a connector portion associated therewith; and
    an elongate cord retainer member having first and second ends, the cord retainer member having a generally rounded cross-sectional configuration, with each of the first and second ends of the cord retainer member being connected to a connector portion of the brow bar member, and the cord retainer member is substantially non-elastic.

2. The eye wear of claim 1, wherein: the brow bar member is curved, whereby the brow bar member closely conforms to the shape of the forehead of the person wearing the eye wear; and the cord retainer member is flexible and is adapted to closely conform to the shape of the temples of the person wearing the eye wear.

3. The eye wear of claim 1, including a sweat bar member disposed on the brow bar member, and adapted to be disposed in an abutting relationship with the forehead of the person wearing the eye wear.

4. The eye wear of claim 1, wherein the at least one lens is curved, whereby the at least one lens closely conforms to the shape of the forehead of the person wearing the eye wear.

5. The eye wear of claim 1, wherein the at least one lens is a single lens disposed and extending over both eyes of the person wearing the eye wear.

6. The eye wear of claim 1, including a nose piece member associated with the at least one lens.

7. The eye wear of claim 1, wherein the at least one lens includes at least one vent to prevent fogging of the lens during use thereof.

8. The eye wear of claim 1, wherein the at least one lens is formed of a plain glass material.

9. The eye wear of claim 1, wherein the at least one lens is a prescription lens.

10. The eye wear of claim 1, wherein the at least one lens includes a prescription lens attached to the at least one lens.

11. The eye wear of claim 1, wherein the at least one lens is formed of a plastic material.

12. The eye wear of claim 11 wherein the plastic material is a polycarbonate plastic material.

13. The eye wear of claim 1 wherein one of the connector portions associated with the brow bar member is an annular flange disposed upon a reduced neck portion formed on one of the ends of the brow bar member.

14. The eye wear of claim 1 wherein one of the connector portions associated with the brow bar member is a barbed member formed on one of the ends of the brow bar member.

15. The eye wear of claim 1 further including a flexible tubular shaped member, having first and second ends, associated with a connector portion of the brow bar member and one of the ends of the cord retainer member.

16. The eye wear of claim 15, wherein a connector portion of the brow bar member is disposed within the first end of the tubular shaped member, and one of the ends of the cord retainer member is disposed within the second end of the tubular shaped member.

17. The eye wear of claim 1, wherein the cord retainer member includes a releasable locking member disposed intermediate the first and second ends of the cord retainer member and is adapted to permit at least a portion of the cord retainer member to closely conform, in an abutting relationship to the temples and the back of the head of the wearer of the eye wear.

18. The eye wear of claim 17, wherein the locking member frictionally engages the cord retainer member.

* * * * *